United States Patent
McConnell et al.

(10) Patent No.: US 11,304,966 B2
(45) Date of Patent: Apr. 19, 2022

(54) COMPOSITION COMPRISING HMOS FOR PREVENTING OR REDUCING NOCICEPTION

(71) Applicant: Glycom A/S, Hørsholm (DK)

(72) Inventors: Bruce McConnell, La Tour de Peilz (CH); Louise Kristine Vigsnæs, Copenhagen (DK); Sami Damak, Lausanne (CH); Norbert Sprenger, Savigny (CH); Francis Foata, La Conversion (CH)

(73) Assignee: Glycom A/S, Hørsholm (DK)

( * ) Notice: Subject to any disclaimer, the term of this patent is extended or adjusted under 35 U.S.C. 154(b) by 0 days.

(21) Appl. No.: 16/956,511

(22) PCT Filed: Dec. 19, 2018

(86) PCT No.: PCT/IB2018/060344
§ 371 (c)(1),
(2) Date: Jun. 19, 2020

(87) PCT Pub. No.: WO2019/123316
PCT Pub. Date: Jun. 27, 2019

(65) Prior Publication Data
US 2021/0008087 A1 Jan. 14, 2021

(30) Foreign Application Priority Data
Dec. 22, 2017 (DK) .................... PA 2017 00740

(51) Int. Cl.
*A61K 31/702* (2006.01)
*A61P 1/00* (2006.01)
*A61K 31/7016* (2006.01)

(52) U.S. Cl.
CPC ........ *A61K 31/702* (2013.01); *A61K 31/7016* (2013.01); *A61P 1/00* (2018.01)

(58) Field of Classification Search
CPC .................................................. A61K 31/702
See application file for complete search history.

(56) References Cited

U.S. PATENT DOCUMENTS

| | | |
|---|---|---|
| 2012/0171165 A1 | 7/2012 | Buck et al. |
| 2013/0195803 A1 | 8/2013 | German et al. |
| 2013/0251844 A1 | 9/2013 | Sprenger et al. |
| 2015/0004147 A1 | 1/2015 | Ritter |
| 2015/0265661 A1 | 9/2015 | Newburg et al. |
| 2016/0243139 A1* | 8/2016 | Vigsnaes .............. A61K 31/702 514/23 |

FOREIGN PATENT DOCUMENTS

| | | |
|---|---|---|
| WO | 0104341 A1 | 1/2001 |
| WO | 2004026257 A2 | 4/2004 |
| WO | 2007101862 A1 | 9/2007 |
| WO | 2009131537 A1 | 10/2009 |
| WO | 2010105207 A1 | 9/2010 |
| WO | 2010115934 A1 | 10/2010 |
| WO | 2010115935 A1 | 10/2010 |
| WO | 2011005681 A1 | 1/2011 |
| WO | 2011100979 A1 | 8/2011 |
| WO | 2011100980 A1 | 8/2011 |
| WO | 2012007588 A9 | 1/2012 |
| WO | 2012009315 A2 | 1/2012 |
| WO | 2012092160 A2 | 7/2012 |
| WO | 2012113404 A1 | 8/2012 |
| WO | 2012113405 A1 | 8/2012 |
| WO | 2012127410 A1 | 9/2012 |
| WO | 2012155916 A1 | 11/2012 |
| WO | 2012156897 A1 | 11/2012 |
| WO | 2012156898 A1 | 11/2012 |
| WO | 2013044928 A1 | 4/2013 |
| WO | 2013091660 A1 | 6/2013 |
| WO | 2013139344 A1 | 9/2013 |
| WO | 2013148134 A1 | 10/2013 |
| WO | 2013154725 A1 | 10/2013 |
| WO | 2015077233 A1 | 5/2015 |
| WO | 2016/066175 A1 | 5/2016 |
| WO | 2016066175 A1 | 5/2016 |
| WO | 2017/190755 A1 | 11/2017 |
| WO | 2017190755 A1 | 11/2017 |

OTHER PUBLICATIONS

Bienenstock, J. et al., PLOS ONE, "Fucosylated but Not Sialylated Milk Oligosaccharides Diminish Colon Motor Contractions", 2013, vol. 8, issue 10, 9 pages (Year: 2013).*
PCT/IB2018/060344, International Search Report, dated Apr. 10, 2019, pp. 1-6.
PCT/IB2018/060344, Written Opinion of the International Searching Authority, dated Apr. 10, 2019, pp. 1-7.
F. Cervero, "Pathophysiology of visceral pain", Rev Dor. Sao Paulo, April-June vol. 15, May 26, 2014, pp. 133-138.
Angele PM Kerchoffs et. al., Lower Bifidobacteria counts in both duodenal mucosa-associated and fecal microbiota in irritable bowel syndrome patients, World Journal of Gastroenterol, Jun. 21, 2009, pp. 1-6.
Tadasu Urashima et al., Milk Oligosaccharides, Copyright © 2011 by Nova Science Publishers, Inc., 2011, pp. 1-99.
Fernando Cervero, Pathophysiology of visceral pain, Rev Dor. São Paulo, Apr.-Jun. 2014, pp. 1-6.
John Bienenstock et. al., Fucosylated but Not Sialylated Milk Oligosaccharides Diminish Colon Motor Contractions, PLOS ONE vol. 8 Issue 10 e76236, Oct. 2013, pp. 1-10.
European Commission, Information from European Union Institutions, Bodies, Offices and Agencies, Official Journal of the European Union C 401/1, Nov. 25, 2017, pp. 1-15.
Anna Klindworth et. al., Evaluation of general 16S ribosomal RNAgene PCR primers for classical and next-generation sequencing-based diversity studies, Nucleic Acids Research, 2013, vol. 41, No. 1, Aug. 28, 2018, pp. 1-11.
Francesco Resta et. al., Kynurenic acid and zaprinast induce analgesia by modulating HCN channels through GPR35 activation, Neuropharmacology 108 (2016) 136e143, Available online Apr. 27, 2016, pp. 1-8.

(Continued)

*Primary Examiner* — Bahar Craigo
(74) *Attorney, Agent, or Firm* — Kunzler Bean & Adamson (57) ABSTRACT

The application relates to synthetic compositions and methods for preventing or reducing nociception and/or nociceptive sensitivity in a non-infant human. The human is administered a composition comprising 6'-sialyllactose (6'-SL) and/or lacto-N-tetraose (LNT).

22 Claims, 1 Drawing Sheet

(56) References Cited

OTHER PUBLICATIONS

A. M. Schoepfer et. al., Antibodies to flagellin indicate reactivity to bacterial antigens in IBS patients, Neurogastroenterol Motil (2008) 20, 1110-1118, 2008, pp. 1-9.

Jungie Qin et. al., A human gut microbial gene catalogue established by metagenomic sequencing, Nature vol. 464, Mar. 4, 2010, pp. 1-9.

Lena Ohman et. al., Crosstalk at the mucosal border: importance of the gut microenvironment in IBS, Nature vol. 12, Jan. 2015, pp. 1-14.

Francoise Gavini et. al., Differences in the Distribution of Bifidobacterial and Enterobacterial Species in Human Faecal Microflora of Three Different (Children, Adults, Elderly) Age Groups, (Online) Journal homepage: https://www.tandfonline.com/loi/zmeh20, 2001, pp. 1-7.

Robert J. Shulman et. al., Increased Gastrointestinal Permeability and Gut Inflammation in Children With Functional Abdominal Pain and Irritable Bowel Syndrome, NIH Public Access Author Manuscript 153(5): 646-650, Nov. 2008, pp. 1-12.

Lei Zhang et. al., 181 Mast Cells and Irritable Bowel Syndrome: From the Bench to the Bedside, J Neurogastroenterol Motil, vol. 22 No. 2, Apr. 2016, pp. 1-12.

H.M. Staudacher et. al., Comparison of symptom response following advice for a diet low in fermentable carbohydrates (FODMAPs) versus standard dietary advice in patients with irritable bowel syndrome, Journal of Human Nutrition and Dietetics 24, pp. 487-495, 2011, pp. 1-9.

R Spiller et. al., Gudielines on the irritable bowel syndrome: mechanisms and practical management, www.gutjnl.com Gut 2007;56:1770-1798, 2007, pp. 1-29.

Mar Guilarte et. al., Diarrhoea-predominant IBS patients show mast cell activation and hyperplasia in the jejunum, www.gutjnl.com Gut 2007;56:203-209, 2007, pp. 1-7.

Tonya Ward et. al., Towards Health: Recurrent Clostridium Difficile Infection Patients With a Successful Outcome Following RBX2660 Treatment Share Microbiome Similarities With Healthy Individuals, AGA Abstracts S-242 https://www.gastrojournal.org/article/S0016-5085(19)37410-4/pdf, Known about as early as Sep. 21, 2020, pp. 1-1.

Robin Spiller et. al., Postinfectious Irritable Bowel Syndrome, Gastroenterology 2009;136:1979-1988, May 2009, pp. 1-10.

George F. Longstreth et. al., Fucntional Bowel Disorders, Gastroenterology 2006;130:1480-1491, Apr. 2006, pp. 1-12.

Giovanni Barbara et. al., Activated Mast Cells in Proximity to Colonic Nerves Correlate with Abdominal Pain in Irritable Bowel Syndrome, Gastroenterology 2004;126;693-702, Mar. 2204, pp. 1-10.

John T Bassett et. al., A review of irritable bowel syndrome and an update on therapeutic approaches, Expert Opin. Pharmacother (2008) 9(7):1129-1143, 2008, pp. 1-16.

Gene Kim et. al., Methanobrevibacter smithii Is the Predominant Methanogen in Patients with Constipation-Predominant IBS and Methane on Breath, Dig Dis Sci (2012) 57:3213-3218, Published online: May 10, 2012, pp. 1-6.

Shafaq Sikandar et. al., Visceral Pain—the Ins and Outs, the Ups and Downs, Europe PMC Funders Group Author Manuscript Curr Opin Support Palliat Care. Author manuscript, Mar. 2012, pp. 1-18.

Sabine Buhner et. al., Mast cell-nerve axis with a focus on the human gut, journal homepage: www.elsevier.com/locate/bbadis Biochimica et Biophysica Acta 1822 (2012) 85-92, 2011, pp. 1-8.

M. M. Walker et. al., Duodenal mastocytosis, eosinophilia and intraepithelial lymphocytosis as possible disease markers in the irritable bowel syndrome and functional dyspepsia, NIH Public Access Author Manuscript Aliment Pharmacol Ther 29(7): 765-773, Apr. 1, 2009, pp. 1-18.

D. B. A. Silk et. al., Clinical trial: the effects of a trans-galactooligosaccharide prebiotic on faecal microbiota and symptoms in irritable bowel syndrome, Alimentary Pharmacology & Therapeutics Aliment Pharmacol Ther 29, 508-518, Dec. 2008, pp. 1-11.

Xi Chen, Human Milk Oligosaccharides (HMOS): Structure, Function, and Enzyme-Catalyzed Synthesis, Advances in Carbohydrate Chemistry and Biochemistry, vol. 72 ISSN 0065-2318, 2015, pp. 1-78.

* cited by examiner

COMPOSITION COMPRISING HMOS FOR PREVENTING OR REDUCING NOCICEPTION

CROSS-REFERENCE TO RELATED APPLICATIONS

This application is a National Stage Entry under 35 U.S.C. § 371 of International Application PCT/IB2018/060344 filed on Dec. 19, 2018, which claims priority to Danish Patent Application No. PA 2017 00740 filed Dec. 22, 2017, the entirety of which are incorporated herein by reference.

FIELD OF THE INVENTION

This invention relates generally to compositions and methods for preventing or reducing nociception and/or nociceptive sensitivity in a non-infant human.

BACKGROUND TO THE INVENTION

Nociception is the ability to feel pain caused by stimulation of a nociceptor. Nociceptors are widely present in peripheral structures in the body, e.g. the skin, muscle, joints, bone and viscera. The activation of nociceptors results in the peripheral and central nervous system (CNS) processing of information generated by the nociceptors. This information is transmitted to the dorsal horn of the spinal cord, or its trigeminal homologue, the nucleus caudalis. From there, the information continues to the brainstem and ultimately the cerebral cortex, where a perception of pain is generated. Typically, noxious stimuli, including tissue injury, activate the nociceptors. Pain is different in that it is a product of higher brain centre processing, whereas nociception can occur in the absence of pain. For example, the spinal cord of an individual having a complete spinal cord transection can still process information transmitted by nociceptors and perceive pain. However, because the information cannot be transmitted beyond the spinal cord transection, stimulus-evoked pain is unlikely.

Nociceptors are neurons which have a cell body with a peripheral axon and terminal that responds to the stimulus and a central branch that carries the information into the CNS. There are two major classes of nociceptors that respond to different modalities of noxious stimuli. The largest group of nociceptors is associated with unmyelinated axons, also called C-fibres, that conduct slowly and that respond to noxious thermal, mechanical, or chemical stimulation. Proteins in the membrane of these nociceptors transduce energy into electrical impulses, which in turn are propagated along the peripheral and central axon of the nociceptor into the CNS (the spinal cord for the body and the trigeminal nucleus for the head). The second major nociceptor population is associated with thinly myelinated axons (A-delta fibres). These nociceptors conduct more rapidly than do unmyelinated C-fibres and likely convey "fast" (or sharp) momentary pain, as opposed to slow, diffuse pain, which is transmitted by the C-fibres. All nociceptors have the capacity to become sensitised. When they become more easily excitable (i.e. the threshold for activation is lowered), hyperalgesia (an increased response to a noxious stimulus) with or without allodynia develops and normally innocuous stimuli may provoke nociceptive pain. If these innocuous stimuli characterise a situation of homeostasis under normal conditions, a chronic afferent barrage from the periphery to the spinal cord can occur; resulting in chronic perception of pain. Several animal models of nociception have been used to demonstrate that persistent afferent input to the spinal cord from peripheral sources sustains altered central processing and leads to spontaneous motor abnormalities, hyperalgesia, pain and allodynia.

Nociceptive sensitisation may be a cause of chronic pain in many diseases and conditions. For example, widespread zones of hypersensitivity are present in patients with fibromyalgia, neuropathic pain and irritable bowel syndrome. These regions of hypersensitivity could be maintained, at least in part, by tonic impulses from nociceptive colonic afferent neurons. A potential cause of nociceptive sensitisation in the gastrointestinal tract is an increase of intestinal permeability. This may result in subclinical inflammation, mast cell degranulation, production of proinflammatory cytokines, activation of serotonin-containing enterochromatin cells and activation of T lymphocytes. These mediators may then activate nociceptors. Similar pathways occur for other peripheral nociceptors.

There is generally no cure for conditions involving nociception and current treatments focus on attempting to relieve symptoms; generally using analgesics. However, these treatments have limited efficacy and most patients continue to experience pain. This situation becomes worse in situations of nociceptive sensitisation when medication needs to be taken chronically, which usually results in medication side effects. Therefore, there is a need to provide solutions for managing nociception without side effects; especially in cases of nociceptive sensitivity.

One attempt to address a potential cause of pain using a safe, well tolerated intervention is described in WO 2017/190755. This document discloses synthetic compositions containing one or more human milk oligosaccharides (HMOs) for treating mast-cell mediated, visceral hypersensitivity and/or pain. The human milk oligosaccharides may be selected 2'-FL, 3-FL, DFL, LNnT, LNT, 3'-SL, 6'-SL and LNFP-1, or mixtures of these HMOs. Preferred HMOs are a mix of 2'-FL and LNnT or LNT. The document makes no mention of nociception or reduction of nociceptive sensitisation.

The peripheral receptor GPR35, which is highly expressed in the gastrointestinal tract, has been identified as being involved in the reduction of nociception and nociceptive sensitivity. In particular, activation of GPR35 results in analgesia (Resta et al. *Neuropharmacology* 108, 136 (2016)). Consequently, GPR35 is a target for development of interventions to reduce nociception. Given that nociception is generally chronic and interventions need to be taken chronically, development of safe, well tolerated interventions is a priority.

Therefore, there is a need for a safe, effective intervention for the reduction of nociception and nociceptive sensitivity mediated through mechanisms other than mast-cells.

SUMMARY OF THE INVENTION

In a first aspect, this invention provides a human milk oligosaccharide comprising, consisting of or essentially consisting of 6'-sialyllactose (6'-SL) and/or lacto-N-tetraose (LNT) for use in preventing or reducing nociception and/or nociceptive sensitivity in a non-infant human. Preferably, the prevention or reduction is mediated through receptor GPR35.

In a second aspect, this invention provides a synthetic composition for use in preventing or reducing nociception and/or nociceptive sensitivity in a non-infant human, the composition comprising a human milk oligosaccharide comprising, consisting of or essentially consisting of 6'-sialyl-lactose (6'-SL) and/or lacto-N-tetraose (LNT).

The synthetic composition preferably contains an amount of 0.5 g to 15 g of the 6'-SL and LNT, more preferably 1 g to 10 g. For example, the synthetic composition may contain 2 g to 5 g of the 6'-SL and LNT. The 6'-SL and LNT are preferably present in a ratio of 1:1 to 1:4, for example 1:1.5 to 1:2.5.

Preferably the synthetic composition further comprises one or more other human milk oligosaccharides such as 2'-fucosyllactose (2'-FL), difucosyllactose (DFL) or the mixture thereof.

In a third aspect, this invention provides a method for preventing or reducing nociception and/or nociceptive sensitivity in a non-infant human, the method comprising administering to the non-infant human an effective amount of a human milk oligosaccharide comprising, consisting of or essentially consisting of 6'-sialyllactose (6'-SL) and/or lacto-N-tetraose (LNT).

Preferably, 6'-SL, LNT or the combination thereof is administered in an amount effective to activate GPR35 receptors. The amount administered per day is preferably 0.5 g to 15 g, more preferably 1 g to 10 g per day. For example, 2 g to 5 g of the 6'-SL and/or LNT may be administered per day. The 6'-SL and LNT are preferably administered in a mass ratio of 1:1 to 1:4, for example from 1:1.5 to 1:2.5.

Preferably, the non-infant human is administered the 6'-SL, LNT or the combination thereof for a period of at least 1 week, more preferably for at least 2 weeks, for example at least 4 weeks.

In a fourth aspect, this invention provides a method for the chronic management of nociceptive sensitivity in a non-infant human, the method comprising chronically administering to the non-infant human an effective amount of a human milk oligosaccharide comprising, consisting of or essentially consisting of 6'-sialyllactose (6'-SL) and/or lacto-N-tetraose (LNT). The non-human human is preferably administered the 6'-sialyllactose (6'-SL) and/or lacto-N-tetraose (LNT) daily for a period of at least 4 weeks, more preferably 8 weeks.

Preferably, the 6'-SL and/or LNT is administered in an amount effective to activate GPR35 receptors. The amount of 6'-SL and/or LNT administered per day is preferably 0.5 g to 15 g, more preferably 1 g to 10 g per day. For example, 2 g to 5 g of the 6'-SL and/or LNT may be administered per day.

The non-infant human may additionally be administered one or more other human milk oligosaccharides, for example 2'-fucosyllactose (2'-FL), difucosyllactose (DFL) or the mixture thereof.

The non-infant human may be an irritable bowel syndrome (IBS) patient, a non-coeliac wheat sensitivity (NCWS) patient, a neuropathic pain patient or a fibromyalgia patient.

A fifth aspect of the invention is a pack for use in preventing or reducing nociception and/or nociceptive sensitivity in a non-infant human, the pack comprising at least 14 individual daily doses of an effective amount of a human milk oligosaccharide comprising, consisting of or essentially consisting of 6'-sialyllactose (6'-SL) and/or lacto-N-tetraose (LNT).

The pack preferably contains an amount of 0.5 g to 15 g of the 6'-SL and/or LNT, more preferably 1 g to 10 g. For example, the pack may contain 2 g to 5 g of the 6'-SL and LNT. When present together, the 6'-SL and LNT are preferably present in a mass ratio of 1:1 to 1:4, for example 1:1.5 to 1:2.5. Further, the pack preferably comprises at least about 21 daily doses, for example about 28 daily doses.

A sixth aspect of the invention relates to a method of dietary management of a patient experiencing nociceptive sensitivity, the method comprising administering to the patient an effective amount of a human milk oligosaccharide comprising, consisting of or essentially consisting of 6'-sialyllactose (6'-SL) and/or lacto-N-tetraose (LNT).

DETAILED DESCRIPTION OF THE INVENTION

It has now been surprisingly found that 6'-sialyllactose (6'-SL) and/or lacto-N-tetraose (LNT) activate peripheral GPR35 receptors in non-infant humans. Further, the combination of 6'-SL and LNT acts synergistically to activate GPR35 receptors. This makes 6'-SL and/or LNT ideal for preventing or reducing nociception and/or nociceptive sensitivity given their safety profile as human milk oligosaccharides. Accordingly, this invention provides synthetic compositions comprising 6'-sialyllactose (6'-SL) and/or lacto-N-tetraose (LNT) that may be used in the dietary management of nociception and nociceptive sensitivity in non-infant humans. The compositions are particularly useful for preventing or reducing nociception or nociceptive sensitivity in non-infant patients suffering from functional gastrointestinal diseases such as IBS and non-coeliac wheat sensitivity (NCWS), neuropathic pain or fibromyalgia.

In this specification, the following terms have the following meanings that are applicable to all embodiments described herein, unless specified otherwise:

"Non-infant human" or "non-infant" means a human of 3 years of age and older. A non-infant human can be a child, a teenager, an adult or an elderly person.

"Human milk oligosaccharide" or "HMO" means a complex carbohydrate found in human breast milk (Urashima et al.: Milk Oligosaccharides. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyl-lactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments, a synthetic composition may be, but preferably is not, identical to a naturally occurring composition. The synthetic composition comprises 6'-SL and/or LNT. Also, in some embodiments, the synthetic compositions may comprise one or more nutritionally or pharmaceutically active components which do not affect adversely the efficacy of 6'-SL and/or LNT. Some non-limiting embodiments of a synthetic composition are described below.

"Patient" means an individual suffering from a disease or a pathological condition who is currently or has been in the past put under observation or control by a qualified medical professional.

"Therapy" means treatment given or action taken to reduce or eliminate symptoms of a disease or pathological condition.

"Treat" means to address a medical condition or disease with the objective of improving or stabilising an outcome in the person being treated or addressing an underlying nutritional need. Treat, therefore, includes the dietary or nutritional management of the medical condition or disease by addressing nutritional needs of the person being treated. "Treating" and "treatment" have grammatically corresponding meanings.

"Preventive treatment" or "prevention" means treatment given or action taken to diminish the risk of onset or recurrence of a disease or condition.

"Primary prevention" means prevention of onset of a disease or condition in a patient who is not known to suffer from the disease or condition.

"Secondary prevention" means prevention of onset of the disease or condition in a high-risk individual, or prevention of reoccurrence of symptoms in a patient who already has the condition or disease. "High-risk individual" in the present context means an individual who is not known to suffer from the condition or disease but who has another physiological disease or disorder, such as a GI disorder, that increases the risk of occurrence of the condition or disease.

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of Firmicutes, Bacteroidetes, Actinobacteria, Proteobacteria, Synergistetes, Verrucomicrobia, Fusobacteria, and Euryarchaeota; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is in or attached to the mucous layer covering the epithelium of the gastrointestinal tract, and luminal-associated microbiota, which is found in the lumen of the gastrointestinal tract.

"Enteral administration" means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

"Oral administration" means any conventional form for the delivery of a composition to a human through the mouth. Accordingly, oral administration is a form of enteral administration.

"Nociception" means the ability to perceive pain caused by stimulation of a nociceptor. Nociception (also nociocception or nociperception) is the sensory nervous system's response to certain harmful or potentially harmful stimuli. In nociception, intense chemical (e.g. chili powder in the eyes), mechanical (e.g. cutting, crushing), or thermal (heat and cold) stimulation of sensory nerve cells called nociceptors produces a signal that travels along a chain of nerve fibres via the spinal cord to the brain. Nociception triggers a variety of physiological and behavioural responses and usually results in a subjective experience of pain in sentient beings.

"Nociceptive sensitivity" means a condition in which normally non-noxious stimuli activate nociceptors and generate nociception.

"Dietary management" means exclusive or partial feeding of patients who, because of a disease, disorder or medical condition are suffering from:
  either have a limited, impaired or disturbed capacity to take, digest, absorb, metabolise or excrete ordinary food or certain nutrients contained therein, or metabolites, or
  have other medically-determined nutrient requirements
  (see: Commission Notice on the classification of Food for Special Medical Purposes of the European Commission, *Official Journal of the European Union* C 401, 25 Nov. 2017, p. 10-11).

"Effective amount" means an amount sufficient to render a desired outcome in a human. An effective amount can be administered in one or more doses to achieve the desired outcome.

In accordance with this invention, nociception and/or nociceptive sensitivity can be prevented or reduced in a non-infant human by administering 6'-SL and/or LNT to the human. The 6'-SL and/or LNT may be administered as individual compounds or in the form of a synthetic composition.

Accordingly, one aspect of the invention relates to a human milk oligosaccharide comprising, consisting of or essentially consisting of 6'-sialyllactose (6'-SL) and/or lacto-N-tetraose (LNT) for use in preventing or reducing nociception and/or nociceptive sensitivity in a non-infant human.

Another aspect of this invention is a synthetic composition for use in preventing or reducing nociceptive sensitivity in a non-infant human, the composition comprising a human milk oligosaccharide comprising, consisting of or essentially consisting of 6'-sialyllactose (6'-SL) and/or lacto-N-tetraose (LNT).

Yet another aspect of this invention is a method for preventing or reducing nociception and/or nociceptive sensitivity in a non-infant human, the method comprising administering to the non-infant human an effective amount of a human milk oligosaccharide comprising, consisting of or essentially consisting of 6'-sialyllactose (6'-SL) and/or lacto-N-tetraose (LNT). In one embodiment, the human milk oligosaccharide comprises, consists of or essentially consists of 6'-SL and LNT.

Yet another aspect of this invention is a method for the chronic management of nociceptive sensitivity in a non-infant human, the method comprising chronically administering to the non-infant human an effective amount of a human milk oligosaccharide comprising, consisting of or essentially consisting of 6'-sialyllactose (6'-SL) and/or lacto-N-tetraose (LNT). The non-human human is preferably administered the 6'-sialyllactose (6'-SL) and/or lacto-N-tetraose (LNT) daily for a period of at least 4 weeks, more preferably 8 weeks.

The non-infant human may additionally be administered one or more other human milk oligosaccharides, for example 2'-fucosyllactose (2'-FL), difucosyllactose (DFL) or mixtures thereof. The non-infant human may be an irritable bowel syndrome (IBS) patient, a non-coeliac wheat sensitivity (NCWS) patient, a neuropathic pain patient or a fibromyalgia patient.

Yet another aspect of this invention is a pack for use in preventing or reducing nociception and/or nociceptive sensitivity in a non-infant human, the pack comprising at least 14 individual daily doses of an effective amount of a human milk oligosaccharide comprising, consisting of or essentially consisting of 6'-sialyllactose (6'-SL) and/or lacto-N-tetraose (LNT).

Yet another aspect of this invention is a method of dietary management of a patient experiencing nociceptive sensitivity, the method comprising administering to the patient an effective amount of a human milk oligosaccharide comprising, consisting of or essentially consisting of 6'-sialyllactose (6'-SL) and/or lacto-N-tetraose (LNT).

Yet another aspect of this invention is a use of a human milk oligosaccharide comprising, consisting of or essentially consisting of 6'-sialyllactose (6'-SL) and/or lacto-N-tetraose (LNT) in the dietary management of a patient experiencing nociceptive sensitivity.

Yet another aspect of this invention is a use of a synthetic composition comprising a human milk oligosaccharide comprising, consisting of or essentially consisting of 6'-sialyllactose (6'-SL) and/or lacto-N-tetraose (LNT) in the dietary management of a patient experiencing nociceptive sensitivity.

Yet another aspect of this invention is a use of a pack comprising at least 14 individual daily doses of an effective amount of a human milk oligosaccharide comprising, consisting of or essentially consisting of 6'-sialyllactose (6'-SL) and/or lacto-N-tetraose (LNT) in the dietary management of a patient experiencing nociceptive sensitivity.

Concerning an embodiment in each aspect, 6'-SL may be a single agent for use in preventing or reducing nociception and/or nociceptive sensitivity in a non-infant human, that is no human milk oligosaccharide other than 6'-SL is administered to the non-infant human.

Concerning an embodiment in each aspect, LNT may be a single agent for use in preventing or reducing nociception and/or nociceptive sensitivity in a non-infant human, that is no human milk oligosaccharide other than LNT is administered to the non-infant human.

Concerning an embodiment in each aspect, a mixture containing, consisting of or consisting essentially of 6'-SL and LNT is administered to the non-infant human. The mass ratio in the 6'-SL:LNT mixture is preferably 1:1 to 1:4; for example 1:1.5 to 1:2.5.

Concerning an embodiment in each aspect, a mixture consisting of or consisting essentially of 6'-SL and LNT is administered to the non-infant human, that is no human milk oligosaccharide other than 6'-SL and LNT is administered to the non-infant human.

Concerning another embodiments in each aspect, human milk oligosaccharides other than 6'-SL and/or LNT may be administered to the non-infant human in addition to 6'-SL and/or LNT if it is not specifically excluded.

The HMOs, including 6'-SL and/or LNT, can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. Descriptions of biotechnological methods to make core human milk oligosaccharides, optionally substituted by fucose or sialic acid, using genetically modified *E. coli*. can be found in WO 01/04341 and WO 2007/101862.

In one embodiment, the synthetic composition can be in the form of a nutritional composition. For example, the nutritional composition can be a food composition, a rehydration solution, a medical food or food for special medical purposes, a nutritional supplement and the like. The nutritional composition can contain sources of protein, lipids and/or digestible carbohydrates and can be in powdered or liquid forms. The composition can be designed to be the sole source of nutrition or as a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for humans with inflamed or compromised GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve intestinal barrier function and mucosal healing and the barrier function of the intestine. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably, the composition is free from added lactose. Generally, digestible carbohydrates provide about 35% to about 55% of the energy of the nutritional composition. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for humans with inflamed or compromised GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-3 (n-3) to omega-3 (n-6) ratio of about 4:1 to about 10:1. For example, the n-3 to n-6 fatty acid ratio can be about 6:1 to about 9:1. The polyunsaturated fatty acid may consist of an omega-3 fatty acid.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron. A source of magnesium, for example magnesium dicitrate (600 mg), may reduce migraine occurrence and intensity. The nutritional composition may also include coenzyme Q10.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 µg/ml of lutein. Lycopene can be included in an amount from about 0.001 µg/ml to about 10 µg/ml, preferably about 0.0185 µg/ml to about 5 µg/ml of lycopene. Beta-carotene can comprise from about 0.001 µg/ml to about 10 mg/ml, for example about 0.034 µg/ml to about 5 µg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. *B. animalis* subsp. *lactis* BB-12, *B. lactis* HN019, *B. lactis* Bi07, *B. lactis* W52, *B. infantis* ATCC 15697, *B. bifidum*, *L. rhamnosus* GG, *L. rhamnosus* HNOOI, *L. acidophilus* LA-5, *L. acidophilus* NCFM, *L. brevis* W63, *L. casei* W56, *L. salivarius* W24, *L. fermentum* CECT5716, *B. longum* BB536, *B. longum* AH1205, *B. longum* AH1206, *B. breve* M-16V, *L. reuteri* ATCC 55730, *L. reuteri* ATCC PTA-6485, *L. reuteri* DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-$\beta$), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of 6'SL and/or LNT in the liquid, by weight of the liquid, is from about 0.05% to about 1.5%, including from about 0.1% to about 1.0%, for example from about 0.2% to about 0.5%. When the nutritional product is a concentrated nutritional liquid, it may be preferred that the total concentration of 6'SL and/or LNT in the liquid, by weight of the liquid, is from about 0.1% to about 3.0%, including from about 0.2% to about 2.0%, for example from about 0.4% to about 1.0%.

In another embodiment, the nutritional composition is in a unit dosage form. The unit dosage form can contain an acceptable food-grade carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a human. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

A unit dosage form can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or non-aqueous liquid, containing a predetermined concentration of the mixture. An orally administered composition can include one or more binders, lubricants, inert diluents, flavouring agents, and humectants. An orally administered composition such as a tablet can optionally be coated and can be formulated to provide sustained, delayed or controlled release of the HMO.

The unit dosage form can also be administered by naso-gastric tube or direct infusion into the GI tract or stomach.

The unit dosage form can also include therapeutic agents such as antibiotics, probiotics, a source of magnesium, melatonin, coenzyme Q10, omega-3 polyunsaturated fatty acids, analgesics, and anti-inflammatory agents. The proper dosage of such a composition for a human can be determined in a conventional manner, based upon factors such as the human's condition, immune status, body weight and age. In some cases, the dosage will be at a concentration similar to that found for 6'SL and/or LNT in human breast milk. The required amount would generally be in the range from about 0.5 g to about 15 g per day, in certain embodiments from about 1 g to about 10 g per day, for example about 2 g to about 5 g per day. Appropriate dose regimes can be determined by methods known to those skilled in the art.

In further embodiment, the HMO can be comprised in a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antibiotics, probiotics, analgesics, and anti-inflammatory agents. The proper dosage of these compositions for a human can be determined in a conventional manner, based upon factors such condition, immune status, body weight and age. In some cases, the dosage will be at a concentration similar to that found for the HMOs in human breast milk. The required amount would generally be in the range from about 0.5 g to about 15 g per day, in certain embodiments from about 1 g to about 10 g per day, for example from about 2 g to about 5 g per day. Appropriate dose regimes can be determined by conventional methods.

For preventing or treating nociception and/or nociceptive sensitivity in a non-infant human, the amount of 6'-SL and/or LNT required to be administered will vary depending upon factors such as the risk and severity of the condition, any underlying medical condition or disease, age, the form of the composition, and other medications being administered. However, the required amount can be readily set by a medical practitioner and would generally be in the range from about 0.5 g to about 15 g per day, in certain embodiments from about 1 g to about 10 g per day, for example from about 2 g to about 5 g per day. An appropriate dose can be determined based on several factors, including, for example, body weight and/or condition, the severity of the condition being treated or prevented, other ailments and/or diseases, the incidence and/or severity of side effects and the manner of administration. Appropriate dose ranges may be determined by methods known to those skilled in the art. In one embodiment, the method comprises a first and a second treatment phase. During the first (initial) phase, the dosing can be higher (for example 2 g to 15 g per day, preferably 3 g to 10 g per day). During the second (maintenance) phase, the dosing can be reduced (for example, 1 g to 10 g per day, preferably 2 g to 5 g per day).

The duration of the administration of 6'-SL and/or LNT will vary depending upon factors such as the risk and severity of the medical condition, age, the form of the composition, the dose and other medications being administered. However, the duration can be readily set by a medical practitioner. Generally, a duration of at least a week will be required to sufficiently to impact symptoms. For example, the duration may be for 1 to 3 months. The administration can continue chronically for an indefinite period.

EXAMPLES

Examples are to illustrate non-limiting embodiments the invention.

Example 1

Six human milk oligosaccharides (LNnT, LNT, 2'-FL, DFL, 6'-SL and 3'-SL) are screened for their ability to activate the GPR35 receptor in the PathHunter β-Arresin assay. This assay monitors the activation of GPR35 expressed in cultured cells, using Enzyme Fragment Complementation with β-galactosidase (β-Gal) as the functional reporter. The enzyme is split into two inactive complementary portions, EA and PK, expressed as fusion proteins in the cell. EA is fused to β-Arrestin and PK is fused to GPR35. When the GPR35 is activated and β-Arrestin is recruited to the receptor, PK and EA complementation occurs, restoring β-Gal activity, which is measured using chemiluminescent Detection Reagents.

The GPR35 cell line is expanded from frozen stocks and cultured according to standard procedures. Cells are seeded in a total volume of 20 µl into white walled, 384-well microplates and incubated at 37° C. for the appropriate time prior to testing. All testing is done in duplicate. The HMO samples are held in the form of concentrated stocks in Phosphate Buffered saline (PBS). A 5× dilution compound working intermediate is prepared in PBS. Five µl of the sample is added to the cells and incubated at room temperature for 3 to 5 hours. The assay signal is generated through a single addition of 12.5 µl (50 v/v %) of PathHunter Detection reagent cocktail, followed by one-hour incubation at room temperature. Microplates are read following signal generation with a PerkinElmer Envision™ instrument for chemiluminescent signal detection. Zaprinast (which is known to be an activator of GPR35) is used as positive control. Dose-response is generated by iterative 3× dilutions of the highest concentration tested (10 mM).

LNT activates GPR35 with an $EC_{50}$ of 4.5 mM. 6'-SL activates GPR35 with an $EC_{50}$ of 6.5 mM. No activation of GPR35 is obtained with 3'-SL, 2'-FL, DFL and LNnT. An equimolar mix of LNT and 6'-SL activates GPR35 with an $EC_{50}$ of 2.2 mM. This demonstrates synergy between 6'-SL and LNT. A mixture of all six HMOs at an equimolar ratio is also tested, showing similar results as with the combination of LNT and 6'-SL. This demonstrates that the synergistic effect of LNT and 6'-SL is maintained when mixed with other human milk oligosaccharides.

Example 2

A total of 60 male and female IBS patients are recruited to participate in the study. After a screening visit and run-in period of 1-2 weeks, the patients are selected. The patients are randomized into two groups, each of 30 patients, with one group consuming the treatment product and one group the placebo product for 4 weeks. The treatment product contains 5 grams of a combination of 6'-SL and LNT in a 1:2 ratio. The placebo product contains 5 grams glucose. Both products are in powder form in a unit dosage container.

The patients are eligible to participate if they are at an age between 18-75 years, fulfil definition of IBS-D, IBS-C or IBS-A/M according to the Rome IV criteria for IBS and have a global IBS-SSS score of >174 during the 2 weeks run-in period. All recruited patients are able and willing to understand and comply with the study procedures. Patients are excluded if: they have any known gastrointestinal disease(s) that may cause symptoms or interfere with the trial outcome, in particular lactose intolerance and coeliac disease; they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 1 months prior to the study; consumed antibiotic drugs 1 months prior to the study; consumed on a regular basis any medication that might interfere with symptom evaluation 2 weeks prior to the study; diagnosed with and treated for IBS for more than 10 years; and pregnant or lactating.

At the screening visit, clinical and medical history and concomitant medication is registered. IBS diagnostic criteria are assessed and part 2 of the IBS-SSS questionnaire are completed.

A faecal sample kit is distributed together with the Bristol Stool Form Scale (BSFS) and Bowel Movement Diary (BMD) to be filled in during the 7 days just prior to visit 2. Patients will be asked to register their diet 3 days just prior to visit 2 and will be reminded not to change their usual diet during the study.

At the second visit, eligibility criteria are checked, and eligible subjects are randomised to the three arms in the trial. A physical examination is done and a number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Based on clinical symptoms and data from questionnaires, patients are characterised into one of the three following groups; diarrhoea predominant (IBS-D), constipation predominant (IBS-C) or alternating/mixed (IBS-A/M). This enables allocation of patients from each subgroup into the intervention groups. When allocated to the groups patients are provided with either treatment or placebo products. Sigmoidoscopy is performed, and mucosal biopsies and faecal aspirates taken. Patients are asked about any adverse events and any changes in their usual medication. The BSFS and BMD is collected and new forms, to be filled in daily during the intervention period, are distributed. Faecal samples are collected and equipment for new samples are distributed. Blood samples are collected for routine clinical chemistry and haematology and biomarker analysis. Diet records are collected, and patients are asked to register their diet for 3 days just prior to visit 3. Patients are reminded not to change their usual diet during the study.

At the third visit, a physical examination is performed and a number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Remaining study products and compliance diaries are collected to check compliance. Blood samples are collected for routine clinical chemistry and haematology and biomarker analysis, and sigmoidoscopy is performed, and mucosal biopsies and faecal aspirates taken. Patients are asked about any adverse events and any changes in their usual medication. Faecal samples are collected and equipment for collecting new samples distributed. The BSFS and BMD is collected and new forms, to be filled in during the 7 days just prior to visit 4, are distributed. Diet records are collected, and patients are reminded not to change their usual diet during the study.

The study runs for 4 weeks with the patients consuming either a placebo or a treatment product daily. Patients are instructed to consume the products in the morning with breakfast. Compliance is monitored through the interactive internet enabled system.

At the end of the study, each patient has an exit visit with the medical team. Faecal samples and blood samples are collected and analysed as before. A number of questionnaires (GSRS-IBS, IBS-SSS, HADS, NRS-11, VSI, IBS-QOL and PHQ-15 scales) are answered. Questionnaires are filled in electronically. Those who are unable or unwilling to use the electronic system fill out the questionnaires on paper. Patients are asked about any adverse events and any changes in their usual medication or diet, and The BSFS and BMD is collected.

To assess the microbiota profile, DNA is extracted from faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached (Klindworth et al. *Nucleic Acids Res.* 41, e1 (2013)). These are universal bacterial 16S rDNA primers, which target the V3-V4 region. Following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

Patients consuming the 6'-SL and LNT indicate reduced perception of visceral pain as compared to the placebo group. Further, the patients receiving the 6'-SL and LNT indicate reduced occurrence of headaches; indicating reduction of nociceptive sensitivity.

Example 3

C57Bl6/J mice (Janvier S A, Le Genest St. Isle, France) are kept in polypropylene cages in a temperature-controlled room with a 12-hour dark-light cycle during 1 week before electrodes implantation (see below). Five days after surgery, mice are submitted to daily Water Avoidance Stress (WAS) by placing them individually 1 h during 9 days on a 3×3 cm platform in a 40×40 cm size pool filled with cold tap water up to 1 cm from the top of the platform. Sham WAS consists of placing the animals for 1 h/day on the platform in a waterless pool. Animals have free access to water and food. Specific diets are started 3 days before WAS procedure and continued until the end of experiment. Three groups of 12 mice are randomly assigned to the following nutritional interventions:

Group 1: Control diet (AIN93), sham WAS
Group 2: Control diet (AIN93), WAS
Group 3: Experimental diet (AIN93 supplemented with 0.09% w/v of 6'-SL and 0.18% w/v of LNT), WAS To measure abdominal contractions as an index of pain, mice are equipped with 2 nickel-chrome wire electrodes implanted into the abdominal external oblique muscle and one under the skin of the abdomen. Surgery is performed under xylazine/ketamine anaesthesia (both 1.2 mg, subcutaneously). A small balloon (Fogarty, Edwards Laboratories Inc., Santa Anna, USA) is introduced in the rectum and fixed at the base of the tail. The balloon is progressively inflated from 0 to 0.10 ml, by steps of 0.02 ml. Each step of distension lasts 10 sec alternated with a 5-min recovery period in between without distension. Visceral sensitivity to colorectal distension (CRD) is assessed by abdominal muscle electromyography.

Figure 1:
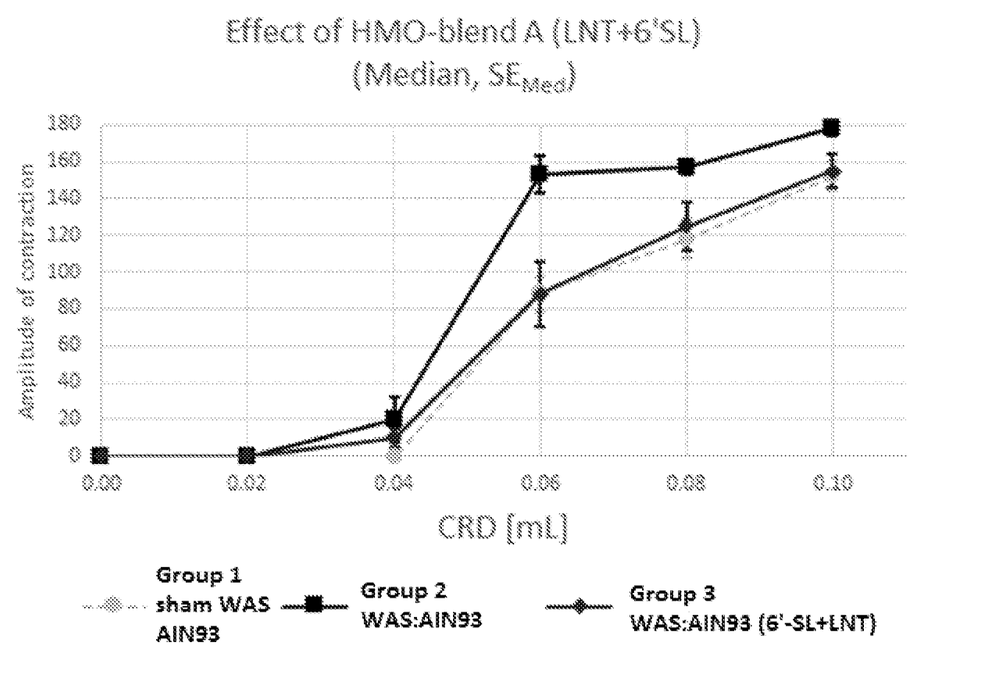
FIG. 1 shows the amplitude of contraction measured as a function of colorectal dilatation in non-sensitized mice (Group 1; dots), in sensitized mice (Group 2; squares) and in sensitized mice to which 6'-SL and LNT are administered (Group 3; diamonds), see Example 3.

The results are shown in FIG. 1. The amplitude of contraction, which is associated with pain perceived by the mice, is significantly increased by the fact that WAS mice are sensitized (Group 2), compared to non-sensitized mice (Group 1). Administration of a mixture of 6'-SL and LNT is able to reduce the amplitude of contraction and thus the perceived pain of sensitized mice (Group 3). For a CRD of 0.06 ml and above, the amplitude of contraction can even not be statistically distinguished from what is observed in non-sensitized mice. A CRD of 0.06 ml corresponds to the typical threshold of pain, whereas smaller dilatation volumes are rather associated with discomfort.

Example 4

Nutritional Composition

A ready to feed nutritional composition is prepared from water, maltodextrin, corn syrup, sugar, milk protein concentrate, vegetable oil (canola, high oleic sunflower and corn), soy protein isolate, acacia gum, flavours, 6'-SL and LNT, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (Stevia), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The composition provides a nutritional supplement which is a good source of protein, low in fat, vitamins, minerals and antioxidants, and meets FODMAP criteria. Further, the composition contains human milk monosaccharides and/or human milk oligosaccharides which are able to promote the growth of beneficial intestinal bacteria and modulate chronic inflammation.

Example 5

Capsule Composition

A capsule is prepared by filling about 1 g of 6'-SL and LNT into a 000 gelatine capsule using a filing machine. The capsules are then closed. The 6'-SL and LNT are in free flowing powder form.

The invention claimed is:

1. A method comprising:
    selecting a non-infant human experiencing nociceptive sensitivity;
    selecting an effective amount of one or more human milk oligosaccharides ("HMOs") chosen from the group consisting of 6'-sialyllactose (6'-SL), and a mixture of 6'-SL and lacto-N-tetraose (LNT); and
    reducing the nociceptive sensitivity by administering the selected effective amount of the chosen HMOs to the non-infant human during a selected administration period.

2. The method of claim 1, further comprising activating GPR35 receptors by administering the effective amount of the chosen one or more HMOs.

3. The method of claim 1, wherein the effective amount of the chosen one or more HMOs administered per day is a total of from 1 g to 10 g per day.

4. The method of claim 1, the method further comprising reducing the occurrence of headaches in the non-infant human by administering the selected effective amount of the chosen one or more HMOs.

5. The method of claim 1, wherein the selected effective amount of the chosen HMOs are administered daily to the non-infant human and the selected administration period is at least four weeks.

6. The method of claim 1, wherein:
the selected effective amount of the one or more HMOs consists of the mixture of 6'-SL and LNT;
the mixture of 6'-SL and LNT is administered in a mass ratio of from 1:1 to 1:4; and
the mixture of 6'-SL and LNT provides a synergistic effect relative to each of the 6'-SL and LNT alone.

7. The method of claim 6, further comprising administering one or more additional HMOs other than 6'-SL or LNT to the non-infant human, while substantially maintaining the synergistic effect.

8. The method of claim 7, wherein the one or more additional HMOs are selected from 2'-fucosyllactose (2'-FL), 3'-sialyllactose (3'-SL), difucosyllactose (DFL), lacto-N-neotetraose (LNnT), and a mixture thereof.

9. A method comprising:
selecting a non-infant human experiencing fibromyalgia and associated nociceptive sensitivity;
selecting an effective amount of one or more human milk oligosaccharides ("HMOs") chosen from the group consisting of 6'-sialyllactose (6'-SL) and a mixture of 6'-SL and lacto-N-tetraose (LNT); and
reducing the nociceptive sensitivity associated with the fibromyalgia by administering the selected effective amount of the chosen HMOs to the non-infant human during a selected administration period.

10. The method of claim 9, further comprising activating GPR35 receptors by administering the effective amount of the chosen one or more HMOs.

11. The method of claim 9, wherein the effective amount of the chosen one or more HMOs administered per day is a total of from 1 g to 10 g per day.

12. The method of claim 9, wherein:
the selected effective amount of the one or more HMOs consists of the mixture of 6'-SL and LNT; and
the mixture of 6'-SL and LNT provides a synergistic effect relative to each of the 6'-SL and LNT alone.

13. The method of claim 12, wherein the mixture of 6'-SL and LNT is administered in a mass ratio of from 1:1 to 1:4.

14. The method of claim 13, further comprising administering one or more additional HMOs other than 6'-SL or LNT to the non-infant human, while substantially maintaining the synergistic effect.

15. The method of claim 14, wherein the one or more additional HMOs are selected from 2'-fucosyllactose (2'-FL), 3'-sialyllactose (3'-SL), difucosyllactose (DFL), lacto-N-neotetraose (LNnT), and a mixture thereof.

16. A method comprising:
selecting a non-infant human experiencing non-celiac wheat sensitivity and associated nociceptive sensitivity;
selecting an effective amount of one or more human milk oligosaccharides ("HMOs") chosen from the group consisting of 6'-sialyllactose (6'-SL) and a mixture of 6'-SL and lacto-N-tetraose (LNT); and
reducing the nociceptive sensitivity associated with the non-celiac wheat sensitivity by administering the selected effective amount of the chosen HMOs to the non-infant human during a selected administration period.

17. The method of claim 16, further comprising activating GPR35 receptors by administering the effective amount of the chosen one or more HMOs.

18. The method of claim 16, wherein the effective amount of the chosen one or more HMOs administered per day is a total of from 0.5 g to 15 g per day.

19. The method of claim 16, wherein the selected effective amount of the chosen HMOs are administered daily to the non-infant human and the selected administration period is at least four weeks.

20. The method of claim 19, wherein:
the selected effective amount of the one or more HMOs consists of the mixture of 6'-SL and LNT; and
the mixture of 6'-SL and LNT provides a synergistic effect relative to each of the 6'-SL and LNT alone.

21. The method of claim 16, further comprising administering one or more additional HMOs other than 6'-SL or LNT to the non-infant human, while substantially maintaining the synergistic effect.

22. The method of claim 20, wherein the mass ratio of the 6'-SL to the LNT in the mixture is from 1:1 to 1:4.

* * * * *